US010100024B2

(12) United States Patent
Stochniol et al.

(10) Patent No.: US 10,100,024 B2
(45) Date of Patent: Oct. 16, 2018

(54) PROCESS FOR THE EPOXIDATION OF AN OLEFIN

(71) Applicant: Evonik Degussa GmbH, Essen (DE)

(72) Inventors: Guido Stochniol, Haltern am See (DE); Wolfgang Wöll, Maintal (DE); Franz Schmidt, Frankfurt (DE)

(73) Assignees: EVONIK DEGUSSA GMBH, Essen (DE); THYSSENKRUPP INDUSTRIAL SOLUTIONS AG, Essen (DE)

( * ) Notice: Subject to any disclaimer, the term of this patent is extended or adjusted under 35 U.S.C. 154(b) by 0 days.

(21) Appl. No.: 15/329,626

(22) PCT Filed: Jul. 23, 2015

(86) PCT No.: PCT/EP2015/066814
§ 371 (c)(1),
(2) Date: Jan. 27, 2017

(87) PCT Pub. No.: WO2016/016070
PCT Pub. Date: Feb. 4, 2016

(65) Prior Publication Data
US 2017/0210718 A1 Jul. 27, 2017

(30) Foreign Application Priority Data
Jul. 29, 2014 (EP) .................................... 14178860

(51) Int. Cl.
C07D 301/12 (2006.01)
C07D 303/04 (2006.01)

(52) U.S. Cl.
CPC ......... C07D 301/12 (2013.01); C07D 303/04 (2013.01)

(58) Field of Classification Search
CPC ............................. C07D 301/12; C07D 303/04
See application file for complete search history.

(56) References Cited

U.S. PATENT DOCUMENTS

| 4,410,501 | A | 10/1983 | Taramasso | |
|---|---|---|---|---|
| 5,675,026 | A | 10/1997 | Thiele | |
| 6,372,924 | B2 | 4/2002 | Thiele | |
| 6,491,861 | B1 | 12/2002 | Grosch et al. | |
| 6,710,002 | B2 | 3/2004 | Grosch | |
| 6,756,503 | B2 | 6/2004 | Teles et al. | |
| 6,849,162 | B2 | 2/2005 | Teles et al. | |
| 7,157,610 | B2 | 1/2007 | Hofen et al. | |
| 7,169,945 | B2 | 1/2007 | Haas et al. | |
| 7,527,712 | B2 | 5/2009 | Bassler et al. | |
| 8,735,612 | B2 * | 5/2014 | Crampton | B01J 29/89 549/512 |

| 2004/0110970 | A1 | 6/2004 | Haas et al. |
|---|---|---|---|
| 2009/0137851 | A1 | 5/2009 | Pottast et al. |
| 2013/0023683 | A1 | 1/2013 | Ruwwe et al. |
| 2014/0228589 | A1 | 8/2014 | Stepp et al. |
| 2018/0134676 | A1 | 5/2018 | Jahn et al. |

FOREIGN PATENT DOCUMENTS

| EP | 0 100 119 | 2/1984 |
|---|---|---|
| EP | 0 230 949 | 8/1987 |
| EP | 0 712 852 | 5/1996 |
| EP | 0 814 058 | 12/1997 |
| EP | 1 247 805 | 10/2002 |
| RU | 2159675 | 11/2000 |
| WO | WO 97/47614 | 12/1997 |
| WO | WO 00/76989 | 12/2000 |
| WO | WO 01/57010 | 8/2001 |
| WO | WO 02/085873 | 10/2002 |
| WO | WO 03/093255 | 11/2003 |
| WO | WO 2004/048335 | 6/2004 |
| WO | WO 2005/000827 | 1/2005 |
| WO | WO 2006/001876 | 1/2006 |
| WO | WO 2008/151742 | 12/2008 |
| WO | WO 2007/074101 | 3/2010 |
| WO | WO 2011/064191 | 6/2011 |
| WO | WO 2011/119215 | 9/2011 |

OTHER PUBLICATIONS

International Search Report for PCT/EP2015/066814 filed Jul. 23, 2015.
Written Opinion of the International Searching Authority for PCT/EP2015/066814 filed Jul. 23, 2015.
International Preliminary Report on Patentability (under chapter II) for PCT/EP2015/066814, filed Jul. 23, 2015 and including a Written Reply to the Written Opinion filed by the Applicant during international stage.
European Search Report and Opinion for EP 14 17 8860 filed Jul. 29, 2014.
U.S. Appl. No. 15/570,167, filed Oct. 27, 2017, Jahn.
Office Action for copending U.S. Appl. No. 15/570,167, dated Feb. 20, 2018.
Kuo, Alex C.M., Poly(dimethylsiloxane), in *Polymer Data Handbook*, 411-435 (1999).
Response to Office Action for copending U.S. Appl. No. 15/570,167, filed May 28, 2018.
U.S. Appl. No. 15/778,318, filed May 23, 2018, Brendel, et al.
U.S. Appl. No. 15/778,337, filed May 23, 2018, Pascaly, et al.
U.S. Appl. No. 15/778,425, filed May 23, 2018, Hofen, et al.
U.S. Appl. No. 15/778,562, filed May 23, 2018, Wiederhold, et al.

* cited by examiner

Primary Examiner — Timothy R Rozof
(74) Attorney, Agent, or Firm — Law Office of: Michael A. Sanzo, LLC

(57) ABSTRACT

In a process for the epoxidation of an olefin, where a mixture comprising olefin, hydrogen peroxide, water and methanol with a weight ratio of water to methanol of less than 1 is passed through a catalyst fixed bed comprising a shaped titanium silicalite catalyst, catalyst breakage is reduced by conditioning the dry catalyst with at least one conditioning liquid comprising water and from 25 to 45% by weight methanol.

20 Claims, No Drawings

PROCESS FOR THE EPOXIDATION OF AN OLEFIN

CROSS REFERENCE TO RELATED APPLICATIONS

The present application is US national stage of international application PCT/EP2015/066814, which had an international filing date of Jul. 23, 2015, and which was published in English under PCT Article 21(2) on Feb. 4, 2016. The application claims priority to European application 14178860.4, filed on Jul. 29, 2014. The priority application is hereby incorporated by reference in its entirety.

The present invention is directed to a process for the epoxidation of an olefin using a shaped titanium silicalite catalyst arranged in a catalyst fixed bed.

The epoxidation of olefins with hydrogen peroxide in the presence of a titanium silicalite catalyst is known from EP 100 119 A1. The epoxidation is carried out in the liquid phase and methanol has turned out to be the preferred solvent, providing high reaction rates and epoxide selectivities.

For a technical use, the titanium silicalite catalyst is preferably employed as a shaped catalyst arranged in a catalyst fixed bed. The methods for preparing a shaped titanium silicalite catalyst in general employ a binder and a calcination step and provide dry, shaped titanium silicalite catalysts.

The prior art methods for epoxidizing an olefin with hydrogen peroxide and a shaped titanium silicalite arranged in a catalyst fixed bed usually start out with a dry, extruded catalyst and pass a mixture containing olefin and hydrogen peroxide in a methanol solvent over the catalyst bed without any prior conditioning of the catalyst, such as disclosed in WO 00/76989, EP 1 085 017 A1 or EP 1 247 805 A1. WO 97/47614 describes washing the fixed bed catalyst with methanol solvent before starting the epoxidation reaction.

WO 98/55228 discloses a method of regenerating a zeolite catalyst by calcination at 250 to 800° C. and the use of the regenerated zeolite catalyst for an epoxidation of olefins. The regeneration method of WO 98/55228 comprises a step of cooling the calcined catalyst in an inert gas stream and the document teaches to cool slowly, because rapid cooling may negatively affect the mechanical hardness of the catalyst. The document further teaches that rapid purging of the regenerated, dry, shaped catalyst during restart of the reactor for further reaction may negatively affect the mechanics of the catalyst. WO 98/55228 proposes in this context to add a liquid vapor to the inert gas stream used in the cooling step in an amount of up to 20% by volume and teaches water, alcohols, aldehydes, ketones, ethers, acids, esters, nitriles and hydrocarbons as suitable, with water and alcohol being preferred.

The inventors of the current invention have now observed that contacting a dry extruded catalyst with methanol or an epoxidation reaction feed rich in methanol can lead to rupture of the extrudates leading to reduced efficiency of the catalyst when employed in a catalyst fixed bed. The inventors have further observed that catalyst breakage is reduced if the dry extruded catalyst is first contacted with an aqueous medium having a low content of methanol and the methanol content is thereafter increased to the level present in the epoxidation reaction feed.

Subject of the invention is therefore a process for the epoxidation of an olefin, comprising the steps:
a) providing a dry, shaped titanium silicalite catalyst;
b) contacting said catalyst with a first conditioning liquid comprising more than 60% by weight water and less than 40% by weight methanol to provide a conditioned catalyst;
c) optionally contacting said catalyst subsequent to step b) with at least one further conditioning liquid having a methanol content higher than the methanol content of said first conditioning liquid; and
d) passing a mixture comprising olefin, hydrogen peroxide, water and methanol through a catalyst fixed bed comprising said conditioned catalyst, wherein the weight ratio of water to methanol is less than 1;
wherein at least one of said conditioning liquids comprises water and from 25 to 45% by weight methanol with the combined amount of water and methanol being at least 95% by weight.

In step a) of the process of the invention, a dry, shaped titanium silicalite catalyst is provided. For the purpose of the invention, a dry catalyst is a catalyst containing essentially no water or polar organic solvent comprising a hydroxyl group. In particular, a dry catalyst contains less than 10% by weight of water and polar organic solvents comprising a hydroxyl group, preferably less than 5% by weight. The dry catalyst may be obtained by a calcination step in which the catalyst is heated to a temperature of more than 200° C., preferably to a temperature of from 400 to 1000° C. in order to remove volatile or organic decomposable components. The dry catalyst may alternatively be obtained by a thermal regeneration of a used catalyst, preferably a catalyst that has been used in an epoxidation reaction. Thermal regeneration may be carried out by subjecting a used catalyst to a temperature of from 200 to 600° C., preferably from 250 to 500° C. Thermal regeneration is preferably carried out with passing a gas stream over the catalyst in order to remove volatile components. The gas stream may be an inert gas, such as nitrogen or water vapor, or may be an oxygen containing gas stream, such as air or oxygen depleted air for removing deposits by oxidation. The dry, shaped titanium silicalite catalyst is preferably provided in step a) at a temperature of from 0 to 100° C.

For the purpose of the invention, a shaped titanium silicalite catalyst is a catalyst obtained by shaping a titanium silicalite powder to form larger particles or objects, preferably having an essentially uniform geometry.

Shaping can be carried out by any method known from the prior art for shaping a titanium silicalite powder. Preferably, the shaped titanium silicalite catalyst is prepared by an extrusion process where a kneadable mass of a titanium silicalite powder, a liquid, a binder or binder precursor, and optionally processing additives is pressed through a die, the formed strands are cut, dried to green bodies and calcined to form extrudates. The shaped titanium silicalite catalyst is therefore preferably in the form of extrudates, preferably having a cylindrical shape, where the edges at the end of the cylinders may optionally be rounded. The cylinders of such shaped catalyst preferably have a diameter of from 1 to 5 mm and a length of from 2 to 7 mm. The extrudates preferably comprise a silica binder. Suitable binder precursors for a silica binder that can be used in an extrusion process are fumed or precipitated silicas, silica sols, silicone resins or silicone oils, such as polydimethylsiloxanes, and tetraalkoxysilanes, such as tetraethoxysilane. Shaping can be carried out with a calcined titanium silicalite powder or with an uncalcined titanium silicalite powder still containing template molecules within the zeolite framework. When shaping is carried out with an uncalcined titanium silicalite powder, the catalyst is calcined after shaping in order to remove the template from the zeolite framework.

The titanium silicalite preferably has a MFI or MEL crystal structure and a composition $(TiO_2)_x(SiO_2)_{1-x}$ where x is from 0.001 to 0.05. Methods for making such a titanium silicalite are known from the prior art, for example from U.S. Pat. No. 4,410,501 and EP 814 058.

The dry, shaped titanium silicalite catalyst is preferably provided in the catalyst fixed bed that is used for reacting olefin with hydrogen peroxide in step d) of the process of the invention. The dry, shaped titanium silicalite catalyst may be provided in the catalyst fixed bed by filling dry, shaped titanium silicalite catalyst into a reactor to form a catalyst fixed bed or it may be provided by thermal regeneration of the catalyst fixed bed that has been used in step d) of the process of the invention.

In step b) of the process of the invention, the dry, shaped titanium silicalite catalyst is contacted with a first conditioning liquid comprising more than 60% by weight water and less than 40% by weight methanol to provide a conditioned catalyst. The first conditioning liquid preferably comprises more than 70% by weight water and less than 30% by weight methanol, more preferably at least 75% by weight water and no more than 25% by weight methanol and most preferably does not comprise any methanol. Preferably, the first conditioning liquid does not contain any further solvents in addition to water and methanol. The use of a first conditioning liquid containing no methanol or further solvents in addition to water has the advantage that no solvent has to be recovered from the first conditioning liquid and that fine particles, present in the dry, shaped titanium silicalite catalyst due to calcination or thermal regeneration, will be removed in step b) and do not interfere with recovery of solvent from conditioning liquid. The first conditioning liquid may contain bases or salts in order to neutralize acidic sites of the catalyst and improve the selectivity for epoxide formation in step d). Suitable bases and salts for such neutralization of acidic sites are known from the prior art, such as EP 230 949, EP 712 852 and EP 757 043.

In a preferred embodiment, the process of the invention further comprises a step c) subsequent to step b) in which the catalyst is contacted with at least one further conditioning liquid having a methanol content higher than the methanol content of said first conditioning liquid. The further conditioning liquid preferably does not contain further solvents in addition to water and methanol.

At least one of the conditioning liquids comprises water and from 25 to 45% by weight methanol with the combined amount of water and methanol being at least 95% by weight. This means that either the first conditioning liquid or at least one of the further conditioning liquids or both the first and at least one of the further conditioning liquids fulfill these conditions. Preferably, at least one of the conditioning liquids comprises water and from 25 to 40% by weight methanol. The use of a conditioning liquid containing methanol in such an amount and a corresponding amount of water reduces breakage of the shaped catalyst, which is believed to be due to a temperature rise caused by adsorption of methanol on the titanium silicalite. If a dry, shaped catalyst is contacted with a first conditioning liquid comprising more than 40% by weight methanol, the temperature rise caused by adsorption of methanol will lead to catalyst breaking and the use of a first conditioning liquid comprising no more than 25% by weight methanol is particularly effective for avoiding catalyst breaking. If the catalyst is first contacted with a conditioning liquid containing no or less than 25% by weight methanol, the methanol content of a subsequently used further conditioning liquid may be higher and up to 45% by weight methanol. However, the catalyst has to be treated at least once with a conditioning liquid containing at least 25% by weight methanol before carrying out step d) in order to reduce catalyst breaking by a temperature rise caused by adsorption of methanol from the mixture of step d).

When the dry, shaped titanium silicalite catalyst is provided in the catalyst fixed bed, the first conditioning liquid is preferably passed through the catalyst fixed bed in step b). Also in step c) the further conditioning liquid is preferably passed through the catalyst fixed bed. In a preferred embodiment, the further conditioning liquid is passed through the catalyst fixed bed and the methanol content of the further conditioning liquid is increased to more than 50% by weight, starting from the methanol content of the first conditioning liquid. Preferably, the methanol content of the further conditioning liquid is increased until the same weight ratio of water to methanol is reached as used in step d) of the process of the invention. The increase of the methanol content of the further conditioning liquid is carried out continuously or stepwise in steps changing the methanol content by no more than 25% by weight at a time. Preferably, a stepwise change changes the methanol content by no more than 10% by weight at a time. The methanol content of the further conditioning liquid is preferably increased at an average change rate in % by weight per hour that is 1 to 50 times the ratio of the volume flow rate of further conditioning liquid passed through said catalyst fixed bed to the volume of the catalyst fixed bed. More preferably, the average change rate in % by weight per hour is 1 to 20 times this ratio and most preferably 1 to 10 times this ratio. For example, when the volume of the catalyst fixed bed is 1 m$^3$ and the volume flow rate of further conditioning liquid is 2 m$^3$/h, the average change rate for the methanol content is most preferably from 2 to 20% by weight per hour. For a stepwise change by 10% by weight at a time, this translates to a step change every 0.5 to 5 hours. For the purpose of the invention, the volume of the catalyst fixed bed shall mean the geometric volume occupied up by the catalyst fixed bed, encompassing both the volume taken up by the catalyst particles or objects themselves and the void volume within and between catalyst particles or objects. Limiting the step size of a stepwise change of methanol content and limiting the average change rate in % by weight per hour will limit the temperature rise effected by the heat of adsorption of methanol on the titanium silicalite and reduces the risk of crack formation and rupture of the shaped catalyst.

The further conditioning liquid is preferably passed through the catalyst fixed bed with a liquid hourly space velocity (LHSV) of from 0.1 to 500 h$^{-1}$, more preferably of from 0.2 to 50 h$^{-1}$ and most preferably of from 1 to 20 h$^{-1}$.

In steps b) and c) of the process of the invention, the temperature of said conditioning liquid is preferably maintained in the range of from 0 to 100° C., more preferably from 20 to 100° C. When the conditioning liquid is passed through the catalyst fixed bed, the catalyst fixed bed is preferably cooled in steps b) and c). Such cooling allows for carrying out step c) with a higher average change rate of the methanol content. The pressure in steps b) and c) is preferably in the range of from 0.1 to 5 MPa, more preferably from 1 to 5 MPa. The pressure is preferably selected to provide a boiling point of methanol that is at least 10° C., more preferably at least 20° C. higher than the maximum temperature of conditioning liquid in steps b) and c). Most preferably, steps b) and c) are carried out at about the same pressure as step d).

In step d) of the process of the invention, a mixture comprising olefin, hydrogen peroxide, water and methanol is passed through a catalyst fixed bed comprising the conditioned catalyst. In this mixture, the weight ratio of water to methanol is less than 1, preferably less than 0.25 and most preferably from 0.01 to 0.2.

The olefin is preferably an unbranched olefin, more preferably an unbranched C2-C6 olefin. The olefin may be substituted, as for example in allyl chloride. Most preferably, the olefin is propene. Propene may be used mixed with propane, preferably with a propane content of 1 to 20% by volume relative to the sum of propene and propane.

Hydrogen peroxide is preferably used in the form of an aqueous solution with a hydrogen peroxide content of 1 to 90% by weight, preferably 10 to 80% by weight and more preferably 30 to 70% by weight. The hydrogen peroxide may be used in the form of a commercially available, stabilised solution. Also suitable are unstabilised, aqueous hydrogen peroxide solutions obtained from an anthraquinone process for producing hydrogen peroxide. Hydrogen peroxide solutions in methanol obtained by reacting hydrogen and oxygen in the presence of a noble metal catalyst in a methanol solvent may also be used.

The methanol is preferably a technical grade methanol, a solvent stream recovered in the work-up of the epoxidation reaction mixture or a mixture of both.

Olefin, hydrogen peroxide and methanol may be introduced into the catalyst fixed bed as independent feeds or one or more of these feeds may be mixed prior to introduction into the catalyst fixed bed.

Preferably, an additional base, preferably ammonia, is fed to the catalyst fixed bed to control the selectivity of the catalyst. The base may be added separately or admixed to one of the above feeds to the reactor. The addition of the base may be at a constant rate. Alternatively, the base may be added to one of the feeds in such an amount as to maintain a constant pH in the feed stream the base is added to.

The olefin is preferably employed in excess relative to the hydrogen peroxide in order to achieve a significant consumption of hydrogen peroxide, the molar ratio of olefin to hydrogen peroxide preferably being chosen in the range from 1.1 to 30. Methanol is preferably used in a weight ratio of 1 to 50 relative to the amount of hydrogen peroxide.

The epoxidation is typically carried out at a temperature of 30 to 80° C., preferably at 40 to 60° C. The pressure within the catalyst fixed bed is maintained at 0.1 to 5 MPa. If the olefin is propene, the pressure is preferably from 1.5 to 3.5 MPa and more preferably kept at a value of 1.0 to 1.5 times the vapour pressure of pure propene at the reaction temperature.

The reactant feed rates and ratios, the reaction temperature and the length of the catalyst fixed bed are preferably selected to provide a hydrogen peroxide conversion of more than 90%, preferably more than 95%.

The catalyst fixed bed is preferably equipped with cooling means and cooled with a liquid cooling medium. The temperature profile within the catalyst fixed bed is preferably maintained such that the cooling medium temperature of the cooling means is at least 40° C. and the maximum temperature within the catalyst fixed bed no more than 60° C., preferably no more than 55° C.

The mixture comprising olefin, hydrogen peroxide, water and methanol is preferably passed through the catalyst fixed bed in down flow mode, preferably with a superficial velocity from 1 to 100 m/h, more preferably 5 to 50 m/h, most preferred 5 to 30 m/h. The superficial velocity is defined as the ratio of volume flow rate/cross section of the catalyst fixed bed. Additionally it is preferred to pass the mixture through the catalyst fixed bed with a liquid hourly space velocity (LHSV) of from 1 to 20 $h^{-1}$, preferably 1.3 to 15 $h^{-1}$. It is particularly preferred to maintain the catalyst bed in a trickle bed state during the epoxidation reaction. Suitable conditions for maintaining the trickle bed state during the epoxidation reaction are disclosed in WO 02/085873 on page 8 line 23 to page 9 line 15.

The reaction mixture obtained in step d) of the process of the invention can be worked up by any method known from the prior art for working up the reaction mixture of an epoxidation of an olefin with hydrogen peroxide. Preferably, the mixture is worked up by separating unconverted olefin and epoxide product to provide a stream comprising water and methanol as the major component and the further conditioning liquid used in step c) is combined with this stream before methanol is separated from this stream.

During the epoxidation the titanium silicalite catalyst may slowly lose catalytic activity. Therefore, the epoxidation reaction is preferably interrupted and the catalyst is regenerated when the activity of the catalyst drops below a certain level. In order to be able to operate the epoxidation process continuously when changing or regenerating the catalyst, two or more catalyst fixed beds may be operated in parallel or in series.

In a preferred embodiment, the catalyst is regenerated by washing with a methanol solvent at a temperature of at least 100° C. Regeneration is preferably performed at a temperature from 100 to 200° C. for a period of 0.5 to 48 hours, more preferably 2 to 24 hours and most preferably 4 to 10 hours. The catalyst is preferably regenerated within the catalyst fixed bed by passing a flow of methanol solvent through the catalyst fixed bed. Preferably the methanol solvent stream is passed through the catalyst fixed bed in down flow mode and most preferably the flow rate is adjusted to maintain a trickle flow in the catalyst fixed bed.

Regeneration by washing with a methanol solvent may be performed at a constant temperature or using a temperature program. When the methanol solvent is passed through the fixed bed, regeneration is preferably started at the temperature used for the epoxidation reaction. The temperature is then raised to at least 100° C. and maintained at a temperature of at least 100° C. for the time necessary to carry out regeneration. Thereafter, the temperature is lowered back to the temperature used for epoxidation. Finally the methanol flow is stopped and the epoxidation is recommenced by starting to feed the mixture comprising olefin, hydrogen peroxide, water and methanol to the catalyst fixed bed. In such a temperature program, raising and lowering of the temperature is preferably performed at a rate of from 5 K/h to 30 K/h.

When the catalyst is regenerated by passing a methanol solvent stream through the catalyst fixed bed, at least a part of the solvent that is passed through the catalyst fixed bed may be reused for regenerating the catalyst without prior purification. Preferably, the methanol solvent is passed through the catalyst fixed bed without reuse for a period of from 2% to 30% of the time used for regeneration. Thereafter, all the methanol solvent that is passed through the catalyst fixed bed is returned to the regeneration, creating a closed loop for washing the catalyst with a methanol solvent for the remainder of regeneration time. This considerably reduces the amount of methanol needed for regenerating the catalyst.

The methanol solvent used for regenerating the catalyst preferably comprises more than 90% by weight methanol and less than 10% by weight water and more preferably more than 97% by weight methanol and less than 3% by weight water. The methanol solvent is preferably a technical grade methanol, a solvent stream recovered in the work-up of the epoxidation reaction mixture or a mixture of both.

Alternatively, the catalyst can be regenerated thermally by heating the catalyst to a temperature of from 200 to 600° C., preferably from 250 to 500° C. The catalyst is preferably regenerated within the catalyst fixed bed by heating the catalyst fixed bed and passing a gas stream comprising from 0.1 to 20% by volume oxygen through the catalyst fixed bed. The gas stream is preferably a mixture of oxygen and nitrogen containing up to 10% by volume of further inert gases, such as argon. The catalyst fixed bed is preferably heated to the regeneration temperature at a rate of from 1 to 100 K/h, maintained at the regeneration temperature for 1 to 500 h and cooled down at a rate of from 1 to 100 K/h while passing the gas stream through the catalyst fixed bed. After such thermal regeneration, steps b) and optionally c) of the process of the invention are carried out to condition the catalyst dried by the thermal regeneration before epoxidation is recommenced in step d).

The following examples illustrate the benefit of conditioning a dry, shaped titanium silicalite catalyst before contacting it with a liquid having a high methanol content.

EXAMPLES

Example 1

Contacting with water.

The experiment was carried out in a cylindrical thermostated vessel having an internal diameter of 3 cm, a thermoelement arranged in the vessel centre and 3 cm above the vessel bottom and a liquid inlet at the bottom of the vessel. 15 g of dry titanium silicalite extrudates having a diameter of 2 to 4 mm and a length of 2 to 5 mm were placed in this vessel to provide a catalyst fixed bed. The vessel was thermostated to 28° C. and the catalyst fixed bed was purged for 15 min with nitrogen. Then 75 ml of methanol were introduced through the liquid inlet at a rate of 50 ml/min to provide complete immersion of the catalyst fixed bed into liquid. After 30 min the methanol was drained and the catalyst fixed bed was dried by purging with a nitrogen stream of 90° C. The catalyst was then removed from the vessel and broken extrudates were separated and weighed. Table 1 gives the maximum temperature rise registered with the thermoelement and the weight fraction of broken extrudates.

Example 2

Contacting with water followed by methanol.

The same vessel was used as in example 1 and the catalyst fixed bed was prepared as in example 1. Then 75 ml of water were introduced through the liquid inlet at a rate of 50 ml/min. After 30 min the water was drained and 75 ml of methanol were introduced through the liquid inlet at a rate of 50 ml/min. After another 30 min the methanol was drained and the catalyst fixed bed was dried and further processed as in example 1. Table 1 gives the maximum temperature rise registered with the thermoelement and the weight fraction of broken extrudates.

Example 3

Conditioning with water and a stepwise increase in methanol content in steps of 50%.

Example 2 was repeated, but between treatment with water and treatment with methanol the catalyst was treated in the same manner with a mixture containing 50% by weight water and 50% by weight methanol.

Example 4

Conditioning with water and a stepwise increase in methanol content in steps of 25%.

Example 3 was repeated, but between treatment with water and treatment with methanol the catalyst was treated successively with mixtures containing 25, 50 and 75% by weight methanol, the remainder being water.

Example 5

Conditioning with water and a stepwise increase in methanol content in steps of 10%.

Example 4 was repeated with mixtures containing 10, 20, 30, 40, 50, 60, 70, 80 and 90% by weight methanol, the remainder being water.

Example 6

Contacting with a mixture of water and methanol containing 50% by weight methanol.

Example 1 was repeated, using a mixture of water and methanol containing 50% by weight methanol instead of pure methanol.

Example 7

Contacting with a mixture of water and methanol containing 25% by weight methanol.

Example 6 was repeated, using a mixture of water and methanol containing 25% by weight methanol.

Example 8

Conditioning with water and a mixture of water and methanol containing 25% by weight methanol.

Example 3 was repeated, but a mixture containing 75% by weight water and 25% by weight methanol was used instead of the mixture containing 50% by weight water and 50% by weight methanol.

Example 9

Conditioning with a mixture of water and methanol containing 25% by weight methanol.

Example 2 was repeated, but a mixture containing 75% by weight water and 25% by weight methanol was used instead of water.

TABLE 1

Maximum temperature rise and weight fraction of broken extrudates

| Example | Methanol content of liquids in % by weight | Maximum temperature rise in K | Weight fraction of broken extrudates in % |
|---|---|---|---|
| 1* | 100 | 18 | 75 |
| 2* | 0/100 | 7 | 88 |
| 3* | 0/50/100 | 2 | 82 |
| 4 | 0/25/50/75/100 | 1 | 19 |
| 5 | 0/10/20/30/40/50/60/70/80/90/100 | 2 | 1 |
| 6* | 50 | 9 | 82 |
| 7 | 25 | 5 | 27 |
| 8 | 0/25/100 |  | 53 |
| 9 | 25/100 |  | 73 |

*Not according to the invention

The invention claimed is:
1. A process for the epoxidation of an olefin, comprising the steps:
   a) providing a dry, shaped titanium silicalite catalyst;
   b) contacting said catalyst with a first conditioning liquid comprising more than 60% by weight water and less than 40% by weight methanol to provide a conditioned catalyst;

c) optionally contacting said catalyst subsequent to step b) with at least one further conditioning liquid having a methanol content higher than the methanol content of said first conditioning liquid; and d) passing a mixture comprising olefin, hydrogen peroxide, water and methanol through a catalyst fixed bed comprising said conditioned catalyst, wherein the weight ratio of water to methanol is less than 1;

wherein at least one of said conditioning liquids comprises water and from 25 to 45% by weight methanol with the combined amount of water and methanol being at least 95% by weight.

2. The process of claim 1, wherein in step a) the dry, shaped titanium silicalite catalyst is provided in said fixed bed.

3. The process of claim 2, wherein in step b) said first conditioning liquid is passed through said catalyst fixed bed.

4. The process of claim 2, wherein in step c) said further conditioning liquid is passed through said catalyst fixed bed.

5. The process of claim 4, wherein further conditioning liquid is passed through said catalyst fixed bed and the methanol content of said further conditioning liquid is increased to more than 50% by weight, starting from the methanol content of said first conditioning liquid, and this increase is continuous or is stepwise in steps changing the methanol content by no more than 25% by weight at a time.

6. The process of claim 5, wherein the methanol content of said further conditioning liquid is increased at an average change rate in % by weight per hour that is 1 to 50 times the ratio of the volume flow rate of further conditioning liquid passed through said catalyst fixed bed to the volume of said catalyst fixed bed.

7. The process of claim 1, wherein in step b) said first conditioning liquid comprises at least 75% by weight water and no more than 25% by weight methanol.

8. The process of claim 1, wherein in steps b) and c) the temperature of said conditioning liquid is maintained in the range of from 0 to 100° C.

9. The process of claim 2, wherein said catalyst fixed bed is cooled in steps b) and c).

10. The process of claim 1, wherein in steps b) and c) the pressure is in the range of from 0.1 to 5 MPa.

11. The process of claim 1, wherein said shaped titanium silicalite catalyst is in the form of extrudates.

12. The process of claim 11, wherein said extrudates have a cylindrical shape with a diameter of from 2 to 5 mm and a length of from 2 to 7 mm.

13. The process of claim 11, wherein said extrudates comprise a silica binder.

14. The process of claim 1, wherein in step d) the weight ratio of water to methanol is less than 0.25.

15. The process of claim 1, wherein in step d) said olefin is propene.

16. The process of claim 7, wherein in step a) the dry, shaped titanium silicalite catalyst is provided in said fixed bed.

17. The process of claim 16, wherein in step b) said first conditioning liquid is passed through said catalyst fixed bed.

18. The process of claim 16, wherein in step c) said further conditioning liquid is passed through said catalyst fixed bed.

19. The process of claim 18, wherein further conditioning liquid is passed through said catalyst fixed bed and the methanol content of said further conditioning liquid is increased to more than 50% by weight, starting from the methanol content of said first conditioning liquid, and this increase is continuous or is stepwise in steps changing the methanol content by no more than 25% by weight at a time.

20. The process of claim 19, wherein the methanol content of said further conditioning liquid is increased at an average change rate in % by weight per hour that is 1 to 50 times the ratio of the volume flow rate of further conditioning liquid passed through said catalyst fixed bed to the volume of said catalyst fixed bed.

* * * * *